United States Patent [19]

Veech

[11] Patent Number: 5,100,677
[45] Date of Patent: Mar. 31, 1992

[54] FLUID THERAPY WITH VARIOUS ORGANIC ANIONS

[76] Inventor: Richard L. Veech, Laboratory of Metabolism, NIAAA, Room 55A, 12501 Washington Ave., Rockville, Md. 20852

[21] Appl. No.: 940,333

[22] Filed: Dec. 17, 1986

Related U.S. Application Data

[63] Continuation-in-part of Ser. No. 810,918, Dec. 18, 1985, abandoned, which is a continuation-in-part of Ser. No. 748,232, Jun. 24, 1985, Pat. No. 4,663,166, which is a continuation-in-part of Ser. No. 623,102, Jun. 22, 1984, abandoned.

[51] Int. Cl.$^5$ ................................................ A61K 33/14
[52] U.S. Cl. .................................... 424/677; 424/678; 424/679; 424/680; 424/681; 424/719; 514/557; 514/578; 514/529; 514/546
[58] Field of Search ............... 514/578, 557, 529, 546; 424/677, 678, 679, 680, 681, 719

[56] References Cited

U.S. PATENT DOCUMENTS 3,993,750  11/1976  Fox ........................................ 424/154

FOREIGN PATENT DOCUMENTS 0108820  11/1982  European Pat. Off. .

OTHER PUBLICATIONS

Kirkendol et al.—Trans. Am. Soc. Artif. Intern. Organs vol. 23 (1977) pp. 399–404.
Kirkendol et al.—Chem. Abst. vol. 88 (1978) p. 479e.
Gerlach—Chem. Abst. vol. 101 (1984) p. 43636h.
Hejkek et al.—Chem. Abst. vol. 90 (1979) p. 109,863t.
Nagy et al.—Chem. Abst. vol. 78 (1973) p. 47685c.

*Primary Examiner*—Sam Rosen

[57] ABSTRACT

Processes and compositions are provided for accomplishing fluid therapy using the anions l-lactate, pyruvate, d-betahydroxybutyrate, acetoacetate, or mixtures of such. The racemic d,l-lactate or acetate anion mixtures heretofore used in fluids are now known not to be desirable because they cause adverse and toxic effects when administered to mammals.

23 Claims, No Drawings

FLUID THERAPY WITH VARIOUS ORGANIC ANIONS

RELATED APPLICATION

This present application is a continuation-in-part of my copending U.S. patent application Ser. No. 810,918, filed Dec. 18, 1985, now abandoned, which in turn is a continuation-in-part of my copending U.S. patent application Ser. No. 748,232, filed June 24, 1985, now U.S. Pat. No. 4,633,166 which in turn is a continuation-in-part of U.S. patent application Ser. No. 623,102 filed June 22, 1984, now abandoned.

BACKGROUND OF THE INVENTION

1. Field of the Invention

This invention lies in the field of fluid therapy in humans, and more particularly in the field of aqueous solutions for parenteral, oral, dialysis, and irrigation therapy which employ at least one of l-lactate anions, pyruvate anions, d- betahydroxybutyrate anions, acetoacetate anions, or mixtures thereof in combination with selected cations.

2. Prior Art

Previously, I have provided improved electrolyte solutions for in vivo and in vitro usage which contain l-lactate and pyruvate anions, and/or d-betahydroxybutyrate and acetoacetate anions in respective defined ratios in combination with defined Na:Cl ratios; see my copending U.S. patent applications Ser. Nos. 748,232 and 747,792, both filed June 24, 1985, and also my copending U.S. patent application Ser. Nos. 747,858 and 748,184, also filed on such date. However, it is now appreciated that the benefits of using l-lactate, pyruvate, d-betahydroxybutyrate, and/or acetoacetate anions need not be restricted by these previously taught relationships of anion pair ratios to Na:Cl ratios.

The prior art indicated in the 37 Background" sections of these earlier patent applications is incorporated by reference into the present application.

Previously, only racemic mixtures of lactate anions containing both d- and l- forms of lactate have been used in aqueous solutions for human parenteral therapy. The other major organic anion used in human parenteral fluids has been acetate. So far as is now known, the natural l-form of lactate anion has heretofore never been used, apart from the unnatural d- form, in human fluid therapy.

Sodium lactate solutions, used in pharmaceutical practices, are not specified in terms of isomeric structure. In the U.S. and British Pharmacopeias, lactate is defined and approval was duly granted for use of the d,l-lactate mixture. Hence, the d,l-lactate is the form used in contemporary pharmaceutical practice. The l-lactate is recognized to be the physiologically predominant form which is metabolized by different pathways and with different effects than is the d-lactate.

The toxicity of d-lactate has been described in humans (see Oh MS et al *N Eng J Med* 301: 249–251, 1979; Perlmutter, DH et al *J Pediatrics* 102: 234–238, 1983; Stolberg, L et al *N Eno J Med* 306: 1344–1348, 1982). Thus, the d- form has now been discovered to cause adverse and toxic effects when administered to mammals. For example, when an aqueous 20 mM/l d-lactate (or d-lactic acid) is administered parenterally to a rat, swelling of brain tissue is observed because the brain takes in the slowly metabolized d-lactate plus an equivalent amount of $K^+$. With continued administration, coma develops, the cerebral edema worsens and death ensues. In contrast, when l-lactate is similarly administered, the differential concentration of l-lactate between intracellular and extracellular fluid does not cause coma or death. For another example, Veech et al. (Veech, RL and Fowler, RC., "Cerebral Dysfunction and Respiratory Alkalosis During Peritoneal Dialysis with d-Lactate Containing Peritoneal Dialysis Fluids". Am. J. Med., 1987 (in press)) points out that the severe recurrent metabolic alkelemia described by Kenamond et al. ("Severe Recurrent Alkalemia in a Patient Undergoing Continuous Cyclic Peritoneal Dialysis". Am. J. Med., 548–550, 1986) was secondary to an encephalopathy caused by the inclusion of d,l-lactate in routine dialysis fluids. Because of such encephalopathological results, parenteral solutions containing the racemic d,l-lactate anions should not be administered for therapeutic purposes.

All previous commercial formulations of fluids for human therapy use lactate or lactic acid in the racemic d,l form as defined in the United States or British Pharmacopeia (see the United States Pharmacopeia 21st edition, January 1985, p 581, 945–946, 1186; United States Pharmacopeia Convention, Rockville, and British Pharmacopeia 1980, p 250, 666, 667, Her Majesty's Stationary Office, London). Sodium d,l-lactate solutions are currently and conventionally used for three major purposes in current medical practice. First, sodium d,l-lactate solution is used parenterally as an alkalinizing agent to correct acidosis. Secondly, it is used in parenteral fluid therapy to normalize the Na:Cl ratio from the 1:1 ratio found in normal saline. Thirdly, it is used as the counter ion in peritoneal dialysis solutions. In addition, it could also be used in current hemodialysis to replace the acetate anion, or, in its $H^+$ form, as an acid to be added to a bicarbonate hemodialysis fluid.

Prior to the teachings contained in my afore referenced USSN 748,232, pyruvate anions d-betahydroxybutyrate anions, and acetoacetate anions in aqueous solution, so far as is now known, were never used in human therapeutic fluids.

BRIEF SUMMARY OF THE INVENTION

This invention relates to a process for accomplishing fluid therapy without encephalopathy or metabolic bone disease and other complications resulting from use of present fluid formulations in a living human involving the introduction into the body of such human an aqueous solution containing at least one permeant monoanionic metabolite selected from the group consisting of l-lactate anions, pyruvate anions, d-betahydroxybutyrate anions, acetoacetate anions, or mixtures of such anions.

Here, l-lactate is defined as that form of lactate anion found in mammalian tissues and designated l or L-lactate. It is identified by its ability to react with $NAD^+$ to form pyruvate in a reaction catalyzed by mammalian lactate dehydrogenase (EC 1.1.1.27). The form of l-lactate which is dextrorotatory in aqueous solution is designated l-(+) while the salts of l-lactate which in aqueous solution are levorotatory are designated l-(−)lactate (see US Dispensatory. Osol, A, Pratt, R, Gennar, AR,, eds. p 658. JR Lippcott. Philadelphia, 1973). Pyruvate and acetoacetate have no sterospecificity.

More particularly, this invention is directed to improved methods and optionally stable fluids for conventional administration to humans such as, (a) oral ingestion of an aqueous solution containing at least one of such anions, or a mixture of such anions, (b) parenteral therapy involving, for example, the intravenous administration of an aqueous solution containing at least one of such anions, or a mixture thereof, (c) dialysis therapy (hemo or peritoneal) using aqueous solutions containing at least one of such anions, (d) dialysis therapy (hemo or peritoneal) where acetic acid is replaced with at least one acid of the group consisting of l-lactate, pyruvate, d-betahydroxybutyrate or acetoacetic acid, preferably l-lactate, and/or (e) irrigation therapy.

One presently preferred such anion comprises l-lactate. Thus, surprisingly, encephalopathy, metabolic bone disease, and many other complications are not only completely avoided by using l-lactate (or one of the other metabolite anions herein identified and used in the practice of this invention) in place of racemic d-l-lactate, but also the substitution of, for example, l-lactate for d-l-lactate, in solutions employed in fluid therapy, does not cause any change in the heretofore known beneficial physiological or pharmacological effectiveness of such fluids.

In general, a solution containing at least one such anion is administerable for generally the same purposes that prior art parenteral fluids or dialysis fluids are used which contain racemic d-l-lactate anions. For examples, such a solution can be used to treat acidosis, dehydration, blood electrolyte depletion, shock, malnutrition, uremia and the like.

Because mixtures of l-lactate anions and pyruvate anions, and mixtures of d-betahydroxybutyrate anions and acetoacetate anions, in solutions each constitute nearequilibrium couples, which can vary widely in concentration under normal physiological conditions, as explained, for example, in my aforereferenced U.S. patent application Ser. No. 748,232, these anions can be employed with little or no adverse side effects in parenteral fluids and the like. Moreover, the therapeutic use of these anion couples (a) tends to maintain a normal plasma milliequivalent ratio of sodium cations to chloride anions, (b) thus tends to prevent hyperchloremic acidosis, and (c) accomplishes electrolyte and fluid and resuscitation therapy. The anions taught by this invention permit one to avoid the known untoward effects of high levels of the d-lactate anion (see Veech, RL, Fowler, RC, op. cited above) or of acetate anion which are now the major organic anions conventionally added to parenteral fluids (See Veech RL. The toxic impact of parenteral solutions on the metabolism of cells: a hypothesis for physiological parenteral therapy. Am J Clin Nutr 44: 519-551, 1986).

Other and further objects, aims, purposes, features, advantages, embodiments, applications, and the like will be apparent to those skilled in the art from the teachings of the present specification taken together with the claims.

DETAILED DESCRIPTION

For the fluid therapy purposes of my present invention, any conventional administration procedure is suitable, although parenteral (particularly intravenous) administration during hemo or peritoneal dialysis is presently preferred.

For example, sodium l-lactate aqueous solutions, which are stable and easily sterilized, can be used in infusion fluids in place of sodium bicarbonate for treatment for acidosis. For example, the bicarbonate may be dissolved immediately before use in the infusion fluid by light agitation and preferably warmed to body temperature. In such a replacement, 1 g sodium bicarbonate corresponds to about 1.33 g sodium l-lactate, and 1 g sodium l-lactate corresponds to about 0.75 g sodium bicarbonate. The bicarbonate or l-lactate solutions are preferably administered diluted with glucose solution or distilled water. The alkalizing action of sodium l-lactate is diminished in severe liver damage since its breakdown is retarded. See, for example, Documenta Geigy 6th ed, pp. 331-332, Geigy, Manchester, 1962.

In practice, the calculation of the quantity of an alkalizing infusion solution required for adults is based on an average value for the water content of the body of 50% by weight and on a uniform intra- and extra-cellular distribution of bicarbonate, l-lactate, d-betahydroxybutyrate, and other aforementioned permeant monovalent anionic metabolites. This method naturally yields only rough figures. The calculation can be simplified by reckoning in milliequivalents desired change in the alkali reserve. For example, in order to increase or decrease the alkali reserve in a patient weighing 70 kg by 5 mEq, a quantity of, for example, l-lactate, bicarbonate or d-betahydroxybutyrate anions of $70 \times 6 \times 0.5 = 210$ mEq must be administered. In order to avoid the danger of an acidosis becoming converted into an alkalosis, it is advisable not to attempt a complete normalization of the alkali reserve by means of an alkalizing solution, and such solutions should never be administered without supplementary potassium.

In children, a higher water content of about 66% must be reckoned with, so that the calculation yields relatively high infusion quantities. The differences between the calculated and observed effects of alkalizing and of acidifying compounds can be considerable since the above approximate calculation ignores a number of important factors.

In diabetic acidosis, many authors consider it is inadvisable to administer large quantities of sodium salts without potassium salts. On the other hand, extremely good results have been reported in the intensive lactate treatment of diabetic coma. There is no doubt that a moderate alkali therapy with l-lactate and/or pyruvate is indicated in diabetic ketosis with very much lowered alkali reserve, since it has been shown that insulin activity is inhibited by acidosis and that acidosis increases the blood sugar. Clearly use of d-betahydroxybutyrate or acetoacetate would not be suitable for use in diabetic ketoacidosis. As those skilled in the art will also appreciate, the ketone bodies would not be appropriate for use in pregnant women.

When using solutions such as "Lactated Ringer's" (see, for example, my aforereferenced USSN 748,232) to replete body water and electrolytes, the 28 mM d,l-lactate of the prior art is replaced with, for example, 28 mM l-lactate. In this way, the Na:Cl ratio, in such an l-lactate solution, is moved, if desired, towards a normal ratio of 1.36 as found in normal human plasma. Thus, hyperchloremic acidosis resulting from large infusions of normal sodium chloride solutions is avoided. The same considerations apply to use of such solutions in dialysis (see, for example, my aforereferenced US patent applications Ser. Nos. 748,232 and 748,184).

Alternatively, in all the present new solutions, d-betahydroxybutyrate anions, for example, can be used alternatively in place of l-lactate anions. Additional benefits may accrue from the use alternate or combined use of pyruvate and acetoacetate.

A preferred application for this invention involves usage of a mixture of anions of l-lactate and pyruvate, or a mixture of anions d-betahydroxybutyrate and acetoacetate, as indicated, in solutions. Under special circumstances, use of one or the other of such anions alone may be preferred, such as in cases of severe reduction of the pyridine nucleotide systems where administration of pyruvate anions may be preferred. In conditions where long stability of mixed aqueous solutions presents a practical problem, use of l-lactate or d-betahydroxybutyrate alone confers stability on the solution and is to be preferred over the currently used d,l-lactate or acetate.

For one example, to correct an acidosis wherein a 70 kg man is 6 mEq below the normal plasma bicarbonate level of 26–30 mEq/L, then 70×6×0.5 or 210 mEq is infused with a fluid of this invention containing bicarbonate anions and l-lactate anions as described hereinbelow, over a 2 to 4 hour period. Other dosages and rates of infusion may be used, if desired, depending on the clinical situation.

For a second example, a liter of solution of the composition of the current Ringer's lactàte (for the composition thereof, see my aforereferenced USSN 748,232) may be infused over a four hour period into a dehydrated 70 kg man with the exception that the d,l-lactate used is replaced with l-lactate.

For a third example, the prior art accomplishment of peritoneal dialysis by infusion into the peritoneum of 2L of a conventional d,l-lactate based or acetate based peritoneal dialysis solution, is changed in that the 35–45 mM d,l-lactate or acetate is altered and replaced by 35–45mM l-lactate. After remaining in the peritoneum for about ½ hour, the fluid is drained off and the process repeated until the blood urea nitrogen (BUN) is decreased to the level desired.

In parenteral therapy, the total concentration of anions selected from the above indicated anion group, a present preference being l-lactate, pyruvate, and/or mixtures thereof, can range from about 0.01 to 2400 millimoles per liter, though larger and smaller quantities can be used depending upon circumstances. The rate of introduction into a human patient, and the dosage used, are generally the same as are conventionally used in solutions containing, for example, d,l-lactate.

A present preference is to employ, for fluid therapy, an aqueous solution wherein the total concentration of l-lactate or pyruvate anions ranges from about 1 Molar to 1 millimolar. In a more preferred form, from about 28 to 45 millimoles (total) of such anions are present (such as in an improved Ringer's lactate or in improved peritoneal dialysis fluids).

Although a solution taught by the present invention may contain either l-lactate or pyruvate alone, as essentially the sole organic metabolic anion, a mixture of l-lactate anions and pyruvate anions may also be used, and similarly a mixture of d-betahydroxybutyrate anions and acetoacetate anions may be used. When such an anion redox couple is employed, it is presently preferred to employ a milliequivalent ratio of l-lactate anions to pyruvate anions in the range from about 20:1 to 1:1, and a milliequivalent ratio of d-betahydroxybutyrate anions to acetoacetate anions in the range from about 6:1 to 0.5:1.

The l-lactic, pyruvic, d-betahydroxybutyric, and acetoacetic acids themselves as such, may be used. For example, such can be used in combination with aqueous bicarbonate anions; for instance, in sodium bicarbonate containing solutions. Also, one can employ, in the starting solutions used in the processes of present invention, aqueous solutions which contain, along with such metabolite anions as taught in this invention, at least one cation selected from the group consisting of sodium, potassium, calcium, magnesium, and ammonium. Preferably, from about 0.01 to 2400 millimoles per liter of such anions are present.

Inorganic physiologically acceptable anions, besides bicarbonate, may also be present, such as chloride, phosphate, and sulfate, if desired, and if such are present, the respective quantities present are preferably similar to corresponding physiologic levels. A difference between the total milliequvalents of the cations present in a solution and the total milliequivalents of the organic anions of the specified group employed in the practice of this invention (l-lactate, pyruvate, d-betahydroxybutyrate, and acetoacetate) can be provided by other physiologically acceptable anions.

It is considered to be physiologically advantageous and it is generally preferred in the practice of this invention, to maintain the levels of the respective organic metabolite anions employed at values which are approximately physiologic. Also, when a mixture of the monocarboxylic metabolic anions is employed in a given solution, it is not necessary to employ redox couple anion pairs since this use of these defined monocarboxylic metabolite anions does not produce the toxic effects resulting from the present use of d,l-lactate or acetate. Further, it appears to be desirable to employ such anionic metabolites in combination with bicarbonate anions in conditions where large volumes of fluid are to be used and administration of calories is not desired, such as in peritoneal dialysis.

Additionally and preferably, such a solution may contain dissolved therein at least one osmotically active, substantially nonionic substance in accord with, for example, teachings for prior art d,l-lactate and acetate containing solutions. Examples of suitable such nonionic substances include glucose (preferred), fructose, glycerol, sorbitol, and the like. Typically, and preferably, such a solution has an osmolarity ranging from about 240 to 2400 mOsmoles/liter.

In addition, formulations containing ionic nutrients, such as l- amino acids, can benefit from the addition of at least one of the metabolite monocarboxylic acid anions taught herein. For example, the acetate anions present in current commercial amino acid formulations (which lead to metabolic bone disease) can be replaced by such anions. See, for example, my copending U.S. patent application Ser. No. 810,916, filed Dec. 18, 1985, and its continuation-in-part application filed on even date herewith, all the teachings of which are entirely incorporated hereinto by reference.

Also preferably, a starting solution used in the practice of this invention has a pH in the range from about 5 to 9, although for the contemplated human usage, a most preferred pH is about 7.4.

Additional cations and anions may be present in a starting solution as taught, for example, in my aforereferenced U.S. Ser. No. 748,232.

Thus, and as indicated above, such a solution can additionally contain bicarbonate anions. The pH of the resulting solution is adjustable to a desired value, such as a preferred value in the range from about 6 to 8.4, by the addition of the hydrogen form of at least one acid selected from the group consisting of l-lactic, d-betahydroxybutyric, acetoacetic, and pyruvic in an amount sufficient to give such desired value. For example, when an anion of an acid such as l-lactic acid, pyruvate acid, d-betahydroxybutyrate acid, or acetoacetic acid is to be added to a bicarbonate containing starting solution, a desired pH of such solution for use in human hemodialysis, or the like, is given by following the formula:

$$pH = pK_{a'} - \log \frac{[HCO_3^-]}{2([HCO_3^-] - [HA])} - \frac{1}{2}$$

where:

HA is the concentration of carboxylic acid in moles/liter, $pK_{a'} = 6.10$ at 38° C. (see Hastings, AB, et al., J. Biol. Chem. 79:183-192, 1928).

In preferred applications of this sort, such as applications which can incorporate from about 28 to 40 mM/l $HCO_3^{31}$, about 2 to 9 mM/l l-lactic, pyruvic, d-betahydroxybutyric acid and/or acetoacetatic acid may generally be added. Such solutions are presently preferred for peritoneal or hemodialysis over existing fluids containing acetic acid or d,l-lactate because of the toxicity of the presently used acids.

Optionally, carbon dioxide may additionally be dissolved in such a solution, for example, in a range such as taught in my aforereferenced U.S. Ser. No. 748,232.

For purposes of practicing the present invention, only when both l-lactate and pyruvate anions are present in a milliequivalent ratio of from about 20:1 to 1:1, and/or both d-betahydroxybutyrate and acetoacetate anions are present in a milliequivalent ratio of from about 6:1 to 0.5:1 are present in admixture in a starting solution, and only when both sodium cations and chloride anions are also present in such a starting solution, then the milliequivalent ratio of $Na^+$ cation to $Cl^-$ anions is always preferably below 1.24 or above 1.6. Thus, the practice of the methods of this invention does not require, in any given starting solution, both members of a redox active, near-equilibrium monocarboxylic acid couple; either member can be used individually. Also, such practice does not require the use of a narrowly specified range of $Na^+$ to $Cl^-$ milliequivalent ratios (when such inorganic ions are both present).

Thus, as taught herein, therapy (including correction of acidosis, dialysis and/or fluid, electrolyte or nutrient replacement, and the like) in accord with the present invention can be accomplished through the use of any one or more of various anions herein taught in a starting solution wherein the cations are selected from among hydrogen, sodium, potassium, calcium, magnesium, and ammonium.

However, in the practice of this invention, preferably only one monoanionic permeant metabolite (l-lactate, pyruvate, d-betahydroxybutyrate, and acetoacetate) is present in a solution at any one time. Thus, improvement in existing parenteral fluids can be achieved by use of l-lactate alone rather than d,l-lactate as is currently used, for example, in ambulatory parential dialysis fluids. The use of l-lactate in conjunction with other inorganic anions, but in the absence of the unstable ketoacid pyruvate, results in a fluid which has as long a chemical stability as the currently used d,l-lactate, but avoids the toxic effects resulting from the inclusion of the unnatural d-isomer. Thus, for example, one class of solutions, which has characteristically long shelf life and stability, contains as anions only l-lactate anions and/or d-betahydroxybutyrate anions and is termed herein Class I for convenience. This class is particularly useful where long term fluid storage is desirable. Another class of solutions, for example, contains as anions only pyruvate anions and/or acetoacetate anions and is termed herein Class II for convenience. Another class of solutions, for example, contains as anions only a mixture of l-lactate anions and pyruvate anions, or only a mixture of d-betahydroxybutyrate anions and acetoacetate anions, which is useful when redox control is desired, and is termed herein Class III for convenience. Table I illustrates various embodiments of such exemplary classes.

TABLE I

| Item No. | Component | Range of Concentration in mMoles/Liter | | |
|---|---|---|---|---|
| | | Class I | Class II | Class III |
| 1 | l-lactate or betahydroxybutyrate | 0.01-2400 | | |
| 2 | pyruvate or acetoacetate | | 0.01-2400 | |
| 3 | l-lactate plus pyruvate and/or d-betahydroxybutyrate and acetoacetate | | | 0.01-2400 |
| 4 | (cations) | $10^{-5}$-$10^{-9}$ | $10^{-5}$-$10^{-9}$ | $10^{-5}$-$10^{-9}$ |
| | (hydrogen) sodium | 0-2400 | 0-2400 | 0-2400 |
| | potassium | 0-1200 | 0-1200 | 0-1200 |
| | calcium | 0-1200 | 0-1200 | 0-1200 |
| | magnesium | 0-1200 | 0-1200 | 0-1200 |
| | ammonium | 0-10 | 0-10 | 0-10 |

Table II describes four classes of physiologic permeant monoanionic metabolite solutions suitable for each of three major fields of application. The genus class is described in Type A solutions of Table II, where d,l-lactate was previously used, and such improved solutions are suitable for use in treatment of certain forms of metabolic acidosis. For oral or parenteral use in resuscitation or the treatment of acidosis or severe fluid loss in diarrhea, the milliosmolarity of the solutions can vary widely from about 240 mOsmoles/L to 4800 mOsmoles/L. Prior art hypertonic sodium chloride solutions or hypertonic Ringer's lactate solutions have been widely used in resuscitation; such solutions can be reformulated as Type A solutions of this invention. Type B solutions of Table II are suitable for rehydration, electrolyte replacement, and/or nutrition. Type C solutions of Table II, are suitable for use as peritoneal dialysis and hemodialysis fluids. Type D solutions can be regarded as being similar in use to Type C solutions, but such include the permeant monoanionic metabolites in their hydrogen form in solutions which contain bicarbonate so as to achieve a desired pH in a manner which avoids the current toxic effects of high levels of acetate or d,l-lactate. These class D solutions are particularly suitable for use where it is desirable to avoid high levels of monocarboxylic acids. By using normal metabolites, these new fluids improve the corresponding prior art fluids, such as Ringer's lactate, hemodialysis fluids, and the like. With appropriate dosage, these fluids are also suitable for oral ingestion, such as under conditions requiring therapy where close patient monitoring is not possible.

For example, one can accomplish treatment of metabolic acidosis or resuscitation with improved sodium l-lactate or other Type A solutions as described in Table II. For treatment of acidosis, initial parenteral administration followed by oral administration is often preferred.

For example, one can accomplish parenteral fluid therapy with improved l-lactated Ringer's-type solutions (Type B) using the present invention in a human patient suffering from fluid, electrolyte, and/or nutritional depletion. Such a fluid may optionally contain non-ionic dissolved nutrients, usually glucose, from 0 to 280 mmoles/liter.

For another example, one can accomplish dialysis fluid therapy with an improved dialysis solution (Type C) using the present invention in a living human patient. The conventional techniques of hemo- and peritoneal dialysis known to the prior art are employable with the improved fluids of this type. Thus, the renal function of a living human patient is replaced at least in part by passing the blood of the patient over one face of a dialysis membrane while a dialysis fluid is passed over the opposite face of such membrane.

In hemodialysis, it is preferable to use a dialysis solution of Type D containing from about 20 to 55 mM/l of bicarbonate anions, such solution also contains a sufficient portion of anions of at least one of said l-lactate, pyruvate, d-betahydroxybutyrate, and/or acetoacetate anions which are derived from the addition to said solution of, respectively, at least one of l-lactic acid, pyruvic acid, d-betahydroxybutyric acid and/or acetoacetic acid in a total amount which is sufficient to produce a pH in the range from about 5.5 to 8.2, such solution also has a milliosmolarity of from about 250 to 310 mOs/l.

Similarly, when peritoneal dialysis is being practiced, a Type D solution containing bicarbonate can be used and the carboxylic metabolite acid material(s) as above described is/are (as the case may be) also present, but here in an amount sufficient to produce a pH ranging from about 5.5 to 7.5. The milliosmolarity ranges from about 280 to 550 mOs/l achieved by disolution in such solution of sufficient nonionic nutrients.

Type D solutions are also adapted for parenteral administration, and for such purposes, a suitable composition of Type D is similar to that above indicated for peritoneal dialysis.

It will be appreciated that the designation mM and mM/l are used herein in their conventional manner to designate millimoles per liter.

TABLE II

| Component | Preferred Solutions (New) units in mMoles/Liter solution | | | |
|---|---|---|---|---|
| | Type A[1] | Type B[2] | Type C[3] | Type D[4] |
| Cations | | | | |
| $Na^+$ | 0–2400 | 130–160 | 130–145 | 130–145 |
| $K^+$ | 0–60 | 2–10 | 0–4 | 0–4 |
| $Ca^{2+}$ | 0–4 | 0.5–2.5 | 0.5–2.0 | 0–2 |
| $Mg^{2+}$ | 0–3 | 0–1.5 | 0–1.0 | 0–1 |
| Anions | | | | |
| $Cl^-$ | 0–2000 | 90–115 | 90–120 | 95–110 |
| $HCO_3^-$ | 0–2000 | 0 | 0–40 | 20–55 |
| $P_i^{-1.8}$ | 0–50. | 0 | 0 | |
| $SO_4^{2-}$ | 0–1.2 | 0 | | |
| d-lactate$^-$ | 0 | 0 | 0 | |
| acetate$^-$ | 0 | 0 | 0 | |

TABLE II-continued

| Component | Preferred Solutions (New) units in mMoles/Liter solution | | | |
|---|---|---|---|---|
| | Type A[1] | Type B[2] | Type C[3] | Type D[4] |
| l-lactate$^-$ | 0–2400 | 0–55 | 0–55 | 0–20 |
| pyruvate$^-$ | 0–2400 | 0–55 | 0–55 | 0–20 |
| d-betahydroxybutyrate$^-$ | 0–2400 | 0–55 | 0–55 | 0–20 |
| acetoacetate$^-$ | 0–2400 | 0–55 | 0–55 | 0–20 |
| Nonanionics | | | | |
| Glucose | 0–278 | 0–280 | 0–240 | 0–240 |
| pH | 5–8.2 | 6.0–7.5 | 5–8.2 | 5.5–8.2 |

Table II Footnotes:

[1] The total amount of l-lactate, pyruvate, d-betahydroxybutyrate, and/or acetoacetate anions present in any given solution ranges from about 0.1 to 2400 mM with the total number of indicated cations present being such as to achieve electrical neutrality. However for most uses, 140-160 mM of total cations and correspondingly 140-160 mM total anions is preferred.

[2] The total amount of l-lactate, pyruvate, d-betabhydroxybutyrate, and/or acetoacetate anions present in any given solution ranges from about 0.1 to 55 mM with the total number of indicated cations present being such as to achieve electrical neutrality. The milliosmolarity ranges from 270 to 450 mOsmoles/Liter.

[3] The total amount of l-lactate, pyruvate, d-betahydroxybutyrate, and/or acetoacetate anions present in any given solution ranges from about 0.1 to 55 mM with the total number of indicated cations present being such as to achieve electrical neutrality. Such a solution preferably also contains sufficient dissolved nonionics (such as glucose) to produce a desired physiological milliosmolarity from about 250 to 600 mOsmoles/Liter.

[4] The total amount of l-lactate, pyruvate, d-betahydroxybutyrate, and/or acetoacetate anions present in any given solution ranges from about 0.5 to 20, and more preferably from about 1-10 mM with the total number of indicated anions present being such as to achieve electrical neutrality. Preferably for hemodialysis, such solutions has a pH ranging from about 5.5 to 8.2.

Optionally, the quantity of nonionics dissolved in such solution is sufficient to achieve from about 280 to 540 milliosmoles per liter when such solutions are used for peritoneal dialysis. Such a solution has a pH ranging from about 5.5 to 7.5.

EMBODIMENTS

The following examples are merely illustrative of the present invention and are not intended as a limitation upon the scope thereof.

EXAMPLES 1–4

The following Table III illustrates particular solutions of this invention:

TABLE III

| | | (Values are in mMoles/Liter) | | |
|---|---|---|---|---|
| Ex. No. | Component | Class I | Class II | Class III |
| 1 | l-lactate[1] | 1000 | | |
| | $Na^+$ | 1000 | | |
| 2 | pyruvate[2] | | 1000 | |
| | $Na^+$ | | 1000 | |
| 3 | l-lactate[3] | | | 900 |
| | pyruvate | | | 100 |
| | $Na^+$ | | | 1000 |
| 4 | l-lactic acid | 5 | | |

Table III footnotes:

[1] For treatment of acidosis see Merck Handbook p 1866 12th edition.

[2] For treatment of acidosis when severe reduction of [$NAD^+$]/[NADH] is present (see USSN 748,232).

[3] For treatment of acidosis when redox balance is desired (see USSN 748,232).

[4] For use as an additive to a bicarbonate containing solution (see USSN 748,232).

EXAMPLES 5–12

Illustrative examples of various physiological abnormalities which are treatable by using various starting solutions of the present invention are shown in Table IV below;

TABLE IV

Exemplary Useages

| Condition Where Useful and solution common name | Fluid Composition Cation(s) | | Anion(s) in mMoles/liter | | Route of Administration, and Dose |
|---|---|---|---|---|---|
| 5. Dehydration (L-lactated Ringers)[1] | $Na^+$ $K^+$ $Ca^{2+}$ | 130 3 1.5 | $Cl^-$ l-lactate$^-$ | 109 28 | Parenteral 500 ml to 3 liters per day depending on severity and cause |
| 6. Peritoneal Dialysis (Dianeal[2] w/1.5% Dextrose, Travenol)[3] | $Na^+$ $Ca^{2+}$ $Mg^{2+}$ | 141 1.75 0.75 | $Cl^-$ l-lactate$^-$ (also dextrose 83) | 101 45 | Intraperitoneal, 4 to 8, 2 liter bags per day |
| 7. Metabolic Acidosis (Isotonic sodium l-lactate solution)[4] | $Na^+$ | 156.1 | l-lactate | 156.1 | Parenteral or oral, 10 ml to 1 L depending on size of patient |
| 8. Cardiac Reperfusion Fluid[5] | $Na^+$ $Ca^{2+}$ $Mg^{2+}$ $K^+$ | 145 0.5 0.75 4 | $Cl^-$ $HCO_3^-$ pyruvate$^-$ (also glucose 10 and $CO_2$ 1.2) | 115 25 11.5 | Intracoronary infusion after cardiac arrest |
| 9. Dehydration and Potassium Loss[6] in Diarrhea, Keto-acidosis or Stress (Improved Darrow's Solution)[7] | $Na^+$ $K^+$ | 120.2 36.2 | $Cl^-$ l-lactate$^-$ (may be diluted with 2 volumes of .278 mMolar glucose for pediatric use) | 104.7 51.7 | Parenteral or oral[8]. |
| 10. Hemodialysis with Bicarbonate and l-lactic acid[9] | $Na^+$ $K^+$ $Ca^{2+}$ $Mg^{2+}$ | 135 2 1.5 0.375 | $Cl^-$ $HCO_3^-$ l-lactic acid | 106.5 33 2 | Hemodialysis without unphysiolocal levels of acetate[10] |
| 11. Electrolyte Replacement HBDH-Ringer's | $Na^+$ $K^+$ $Ca^{2+}$ $Mg$ | 140 10 2.5 1.5 | $Cl^-$ l-lactate d-betahydroxybutyrate | 103 27.5 27.5 | Alternative to Fox's acetate Ringer's for electrolyte replacement[11] |

Table IV Footnotes

[1] Hartmann AF. Theory and practice of parenteral fluid administration. JAMA 1934; 103: 1349-1354.
[2] Dianeal is a trade mark of Travenol Laboratories, Deerfield Illinois
[3] Facts and Comparisons. St. Louis. JB Lippincott, Oct 81-Aug 1983: 35d-53.
[4] Essellier AF, Jeanneret P. Agueous solutions - parenteral infusion therapy. Documenta Geigy 6th edition. Manchester: Geigy, 1962: 324-334
[5] The period of reperfusion of heart following, for example coronary by pass can be critical and may result in permanent heart damage due to excessive calcium loading. Pyruvate is the preferred substrate for heart under these conditions giving maximal efficiency of cardiac work over either glucose plus l-lactate or glucose alone (See Kobayshi K, Neely JR. The control of maximum rates of glycolysis in rat cardiac muscle. Circ Res 1979; 44: 166-175.
[6] Essellier AF, Jeanneret P. Aqueous solutions - parenteral infusion therapy. Documenta Geigy 6th edition. Manchester: Geigy, 1962: 332-333
[7] Darrow and Pratt. JAMA 1950; 143: 365-ff and 432-ff.
[8] Martin et al. JAMA 1951; 147: 24-ff.
[9] See Table XI. Prior Art Hemodialysis Fluids. WO 86/00227
[10] Blood acetate levels above the physiological level of 0.2 mM are associated with metabolic bone disease. Veech RL. Am J Clin Nutr 44: 544, 1986.
[11] Fox CL. JAMA 1952; 148: 827-833.

It is to be understood that the invention is not limited to the features and embodiments hereinabove specifically set forth, but can be carried out in other ways and manners without departure from its spirit.

I claim:

1. A process for accomplishing fluid therapy in a living human in need of such therapy comprising the steps of introducing into the body of such human an aqueous solution containing at least one anion species selected from the group consisting of pyruvate in an amount so that the concentration of pyruvate$^-$ anions in solution is in the range of about .01 to 40 millimoles per liter, l-lactate$^-$, d-betahydroxybutyrate$^-$, acetoacetate$^-$, and at least one cation selected from the group consisting of sodium$^+$ potassium$^+$ magnesium$^{2+}$, hydrogen$^+$, and ammonium$^+$, the total concentration of all of said anions in said solution being in the range from about 0.01 to 2400 millimoles per liter.

2. The process of claim 1 wherein said introducing is accomplished parenterally.

3. The process of claim 1 wherein said total concentration of said anions ranges from about 1 to 1000 millimoles per liter.

4. The process of claim 1 wherein said anions present in said solution comprise l-lactate anions.

5. The process of claim 1 wherein said anions present in said solution comprise pyruvate anions.

6. The process of claim 1 wherein said anions present in said solution comprise d- betahydroxybutyrate.

7. The process of claim 1 wherein said anions present in said solution comprise acetoacetate.

8. The process of claim 1 wherein said anions present in said solution comprise a mixture of l-lactate anions and pyruvate anions.

9. The process of claim 1 wherein said anions present in said solution comprise a mixture of d-betahydroxybutyrate and acetoacetate anions.

10. The process of claim 1 wherein said anions present in said solution comprise a mixture of l-lactate, pyruvate, d-betahydroxybutyrate and acetoacetate anions.

11. The process of claim 1 wherein said solution contains at least one cation selected from the group consisting of sodium, potassium, calcium, magnesium, ammonium, and hydrogen, the total milliequivalent quantity of such cations in said, solution being equal to the total milliequivalent quantity of said anion(s).

12. The process of claim 1 wherein the cations present in said solution comprise sodium.

13. The process of claim 1 wherein said solution contains at least one of the following mixtures:
   (a) l-lactate anions and pyruvate anions in a milliequivalent ratio of from about 20:1 to 1:1, and
   (b) d-betahydroxybutyrate anions and acetoacetate anions in a milliequivalent ratio of from about 6:1 to 0.5:1, and further contains sodium cations and chloride anions, and the milliequivalent ratio of sodium to chloride is either below 1.24 or above 1.6.

14. The process of claim 1 wherein said introducing is accomplished by irrigation.

15. The process of claim 1 wherein said introducing is accomplished by hemodialysis.

16. The process of claim 1 wherein said introducing is accomplished by peritoneal dialysis.

17. The process of claim 1 wherein said introducing is accomplished by oral ingestion.

18. The process of claim 1 wherein said solution additionally contains bicarbonate anions and the pH of said solution is adjusted to a desired value in the range from about 6 to 8.4 by the addition of the hydrogen from of at least one acid.

19. The process of claim 1 wherein said solution additionally contains chloride anions.

20. The process of claim 18 wherein said solution contains chloride anions.

21. A process for accomplishing fluid therapy in a living human in need of such therapy comprising the steps of introducing into the body of such human an aqueous solution containing at least one anion species comprising l-lactate$^-$ and at least one cation selected from the group consisting of sodium$^+$, potassium$^+$, magnesium$^{2+}$, hydrogen$^+$, and ammonium$^+$, the total concentration of said anions in said solution being in the range from about 0.01 to 2400 millimoles per liter.

22. A process for accomplishing fluid therapy in a living human in need of such therapy comprising the steps of introducing into the body of such human an aqueous solution containing at least one anion species comprising d-betahydroxybutyrate$^-$, and at least one cation selected from the group consisting of sodium$^+$ potassium$^+$ magnesium$^{2+}$, calcium$^{2+}$. hydrogen$^+$, and ammonium$^+$, the total concentration of said anions in said solution being in the range from about 0.01 to 2400 millimoles per liter.

23. A process for accomplishing fluid therapy in a living human in need of such therapy comprising the steps of introducing into the body of such human an aqueous solution containing at least one anion species comprising acetoacetate$^-$ and at least one cation selected from the group consisting of sodium$^+$, potassium$^+$. magnesium$^{2+}$, calcium$^{2+}$, and ammonium$^+$, the total concentration of said anions in said solution being in the range from about 0.01 to 2400 millimoles per liter.

* * * * *

UNITED STATES PATENT AND TRADEMARK OFFICE
CERTIFICATE OF CORRECTION

PATENT NO. : 5,100,677
DATED : March 31, 1992
INVENTOR(S) : Richard L. Veech

It is certified that error appears in the above—identified patent and that said Letters Patent is hereby corrected as shown below:

Claim 1, Column 11, line 66, after "magnesium$^{2+}$", insert --calcium$^{2+}$--;

Claim 21, column 14, line 13, after "magnesium$^{2+}$", insert --calcium$^{2+}$--

Title page, item [76], correct the address of Richard L. Veech to

--712 Brent Road, Rockville, MD 20852--

Signed and Sealed this

Third Day of August, 1993

Attest:

MICHAEL K. KIRK

Attesting Officer

Acting Commissioner of Patents and Trademarks